United States Patent
Davidson

(10) Patent No.: US 6,635,872 B2
(45) Date of Patent: Oct. 21, 2003

(54) DEFECT INSPECTION EFFICIENCY IMPROVEMENT WITH IN-SITU STATISTICAL ANALYSIS OF DEFECT DATA DURING INSPECTION

(75) Inventor: Michael J. Davidson, Hillsboro, OR (US)

(73) Assignee: Applied Materials, Inc., Santa Clara, CA (US)

( * ) Notice: Subject to any disclaimer, the term of this patent is extended or adjusted under 35 U.S.C. 154(b) by 342 days.

(21) Appl. No.: 09/828,345

(22) Filed: Apr. 5, 2001

(65) Prior Publication Data

US 2002/0145112 A1 Oct. 10, 2002

(51) Int. Cl.[7] .............................................. H01J 37/00
(52) U.S. Cl. ........................ 250/307; 250/306; 250/310
(58) Field of Search ................................. 250/307, 306, 250/310, 311

(56) References Cited

U.S. PATENT DOCUMENTS 5,761,064 A * 6/1998 La et al. ................ 364/468.17

* cited by examiner

Primary Examiner—Kiet T. Nguyen
(74) Attorney, Agent, or Firm—Christopher G. Talbot; Blakely Sokoloff Taylor & Zafman

(57) ABSTRACT

A method and system for increasing the efficiency and reducing the time required for defect inspection of micro-fabricated structures such as semiconductor wafers, masks or reticles for micro-fabrication, flat panel displays, micro-electro-mechanical (MEMs). In one embodiment a method of inspection of micro-fabricated structures is optimized by statistically analyzing defect data during inspection by collecting defect data during inspection, calculating at least one statistic of the defect data, continuing inspection while the at least one statistic is outside a predetermined range and stopping inspection when the at least one statistic is within the predetermined range.

22 Claims, 6 Drawing Sheets

| Image Number | 0-450 | 451-900 | 901-1350 | 1351-1800 | 1801-2250 | 2251-2700 | 2701-3150 |
|---|---|---|---|---|---|---|---|
| %STD | 16.2 | 5.0 | 3.1 | 2.6 | 2.5 | 1.4 | 0.5 |

FIG. 2

DEFECT INSPECTION EFFICIENCY IMPROVEMENT WITH IN-SITU STATISTICAL ANALYSIS OF DEFECT DATA DURING INSPECTION

BACKGROUND OF THE INVENTION

1. Field of the Invention

This invention relates to methods and systems for use in defect inspection of micro-fabricated structures such as integrated circuit die on semiconductor wafers, masks or reticles for micro-fabrication, flat panel displays, micro-electromechanical (MEMs) devices and the like during and after manufacture. In particular, the invention provides methods and systems for more effectively and efficiently using defect inspection system time and for reducing the average defect inspection time required to determine defect density and other defect statistics.

2. Prior Art

Over the past decade, defect inspection to detect microscopic manufacturing defects has become a standard part of micro-fabrication manufacturing flows, especially for semiconductor wafers. Defect inspection is performed on a statistical sampling basis of the wafers in the manufacturing flow at key defect-prone or particularly defect-sensitive steps. Various types of inspection technology are in use including bright-field optical inspection with, for example, a KLA-Tencor 2138 made by KLA-Tencor of San Jose Calif., darkfield inspection with for example a KLA-Tencor AIT2 also made by KLA-Tencor. More recently e-beam inspection, with for example Odyssey 300 by Schlumberger Technologies Inc. of San Jose or a KLA-Tencor eS20 made by KLA-Tencor, has emerged has an important tool. Each type of inspection technology is usually applied at steps in the semiconductor manufacturing flow where it is best suited to the types of defects most likely to be found.

Wafer inspection systems for patterned wafer inspection usually work as follows. A high powered microscope, traditionally an optical microscope, but more recently a SEM (Scanning Electron Microscope) or electron microscope, is setup under computer control to acquire sequentially images of the area of wafers to be inspected. To minimize the overhead of wafer stage movement and settling time during the inspection process, continuous scanning motion mechanical stages are used. These stages are specifically designed to have very smooth motion in at least one scanning axis to facilitate image or pixelated contrast data acquisition. In the case of an optically based system, a TDI-CCD (Time Delay Integration-Charged Couple Device) image sensor is synchronized with the scanning motion of the continuous scanning stage to acquire images rapidly. In the case of an e-beam inspection system, the scanning motion of the beam is synchronized with the scanning stage motion to acquire images rapidly.

The image or pixelated contrast data that is acquired in this manner is then compared to reference data. Defects are found or detected where there are differences between the reference and the acquired images. The reference images may be derived from CAD data or may simply be images of neighboring cells or die on the wafer or similar wafer being inspected. The sensitivity of the defect inspection process can be controlled by adjusting the image processing parameters that are used to compare the acquired and reference images.

The economic benefits of inspection have been substantial and inspection is generally accepted as having made a significant contribution to the substantial increase in semiconductor wafer manufacturing yields seen in the 1990s. Inspection systems are employed in a number of different applications including:

- process monitoring to flag when a particular process step in the manufacturing flow has increased the number of defects produced above the level normally anticipated at that step;
- problem solving by inspecting so-called short-loop wafers that have only been processed with a subset of the manufacturing process steps in order to facilitate troubleshooting and diagnosis or optimization of a particular subset of process steps and
- during process development-to optimize a new manufacturing process to reduce or eliminate process-specific or systematic defect mechanisms.

In many cases, it is not only the location of individual defects that is the primary goal of defect inspection. Rather it is measuring the defect distribution over the wafer or sub region thereof, and defect density (that is, the number of defects per unit area) of all defects or of a particular type or class of defect. This information is often required to make decisions about the status of manufacturing, the severity of a problem or an issue in process development.

In a production-worthy process, typical defect densities per process step must be extremely low in order for the yield of the whole manufacturing process flow to be good. With several hundreds of individual process steps typical today in an advanced semiconductor wafer manufacturing flows, killer (critical or yield limiting) defect densities per process step usually range from 0.1–0.0001 defects/cm^2 (defects per centimeter squared) or less.

During process development, defect densities can be much higher, for example, up to many thousands of defects/cm^2 if the process is particularly immature or under certain troubleshooting conditions when higher defects densities may have been deliberately induced for diagnostic or characterization reasons. Such defects may include subtle non-killer defects—measured for reasons of improving quality or reliability, for example, metal voids that might migrate and cause reliability failures after the IC is in use in a system.

The throughput or speed of the inspection process is particularly critical when the inspection system is used as part of the manufacturing process flow. It is usually necessary to be able to measure or monitor defect density in under one hour in the production flow. The overall defect inspection system throughput typically scales as a function of the square of the pixel size used. For example, if the pixel linear dimension is halved in order to be able to find smaller defects, the overall inspection speed will decrease by a factor of four assuming that the pixel data rate remains constant.

This square law dependence that throughput has on pixel size is particularly critical for more advanced higher resolution inspection systems such as e-beam and ultraviolet (UV) optical where the frequent need to use smaller pixels slows the inspection speed significantly.

The slow speeds of high-resolution defect inspection, combined with the fact that the minimum wafer surface area that must be inspected to make a statistically significant measurement of defect density is not known ahead of the inspection, results in inefficient use of expensive inspection system time. To ensure a statistically useful result from inspection, relatively larger wafer surface areas must be inspected. The consequence of this inefficiency is longer inspection time, worse inspection system utilization and higher overall inspection cost.

SUMMARY OF THE INVENTION

In view of the above problems, an object of the present invention is to provide a method for reducing average defect inspection time by using in-situ statistical analysis of defect data during the operation of the inspection system to allow, under certain circumstances, time savings by early termination of some defect inspection runs. In accordance with preferred embodiments of the invention, a method of reducing defect inspection time of micro-fabricated structures by statistically analyzing defect data during inspection, the method comprising inspecting the micro-fabricated structures by acquiring pixelated contrast data from the micro-fabricated structures; detecting defects in the micro-fabricated structures by comparing the pixelated contrast data with reference data to create the defect data; calculating at least one statistic of the defect data; continuing inspection while the at least one statistic is outside a predetermined range and stopping inspection when the at least one statistic is within the predetermined range.

A method of reducing defect inspection time of micro-fabricated structures by statistically analyzing defect data during inspection, the method comprising: inspecting the micro-fabricated structures by acquiring pixilated contrast data from the micro-fabricated structures; detecting defects in the micro-fabricated structures by comparing the pixilated contrast data with predetermined reference data to create the defect data; classifying the defect data into one or more classified defect types; calculating at least one defect density of at least one classified defect type; determining a deviation metric of the at least one defect density of the at least one classified defect type; continuing to inspect the micro-fabricated structures while the deviation metric is outside a predetermined range and stopping inspection when the deviation metric is within a predetermined range.

A method for reducing average defect inspection time by statistically analyzing defect data in near real-time from a semiconductor wafer during defect inspection, the method comprising: inspecting the semiconductor wafer to detect defects by acquiring image data of integrated circuit die on the semiconductor wafer; processing the image data to detect defects in the integrated circuit die to create the defect data; classifying the defect data into at least one classified defect types; calculating at least one defect density of the at least one classified defect type; determining a deviation metric of the at least one defect density of the at least one classified defect type; continuing inspection while the deviation metric is outside a predetermined range; stopping inspection when the deviation metric is within the predetermined range.

An efficient wafer defect inspection system comprising: an XY stage disposed to support a wafer for inspection; a microscope disposed to generate image data of the wafer; a detector arranged to supply image data of the wafer from the microscope to an image computer; stored program instructions that execute on the image computer to produce defect data of defects on the wafer; a control computer disposed to control the inspection system, the control computer periodically calculating at least one statistic of the defect data and the control computer stopping inspection when the at least one statistic is within a predetermined range.

In accordance with other preferred embodiments, the invention includes displaying (tabulated or graphically) the data (including defect data, statistical data and defect density data), using optical (including bright field, optical dark field, optical gray field and laser scatter), charged particle beam, e-beam, voltage contrast, focused ion-beam or UV inspection systems to collect the defect data and calculating various statistics or deviation metrics including the standard deviation of the defect density and the standard deviation of the cumulative defect density. Other embodiments include using the calculated statistics to stop the inspection manually and automatically. Yet further embodiments include statistical stopping criteria based on a normalized standard deviation of less than 10% or 20% with relative stability periods of 10%, 25%, 33% or 50% of the inspection time or area.

Other objects, features and description of the drawings and the claims will become apparent to those of skill in the art by reference to the figures and description that follows.

BRIEF DESCRIPTION OF THE DRAWINGS

FIG. 2 is a table with image number and standard deviation data.

DETAILED DESCRIPTION OF THE DRAWINGS

In the following detailed description of the preferred embodiments and other embodiments of the invention, reference is made to the accompanying drawings. It is to be understood that those of skill in the art will readily see other embodiments and changes may be made without departing from the scope of the invention.

Figure 1:
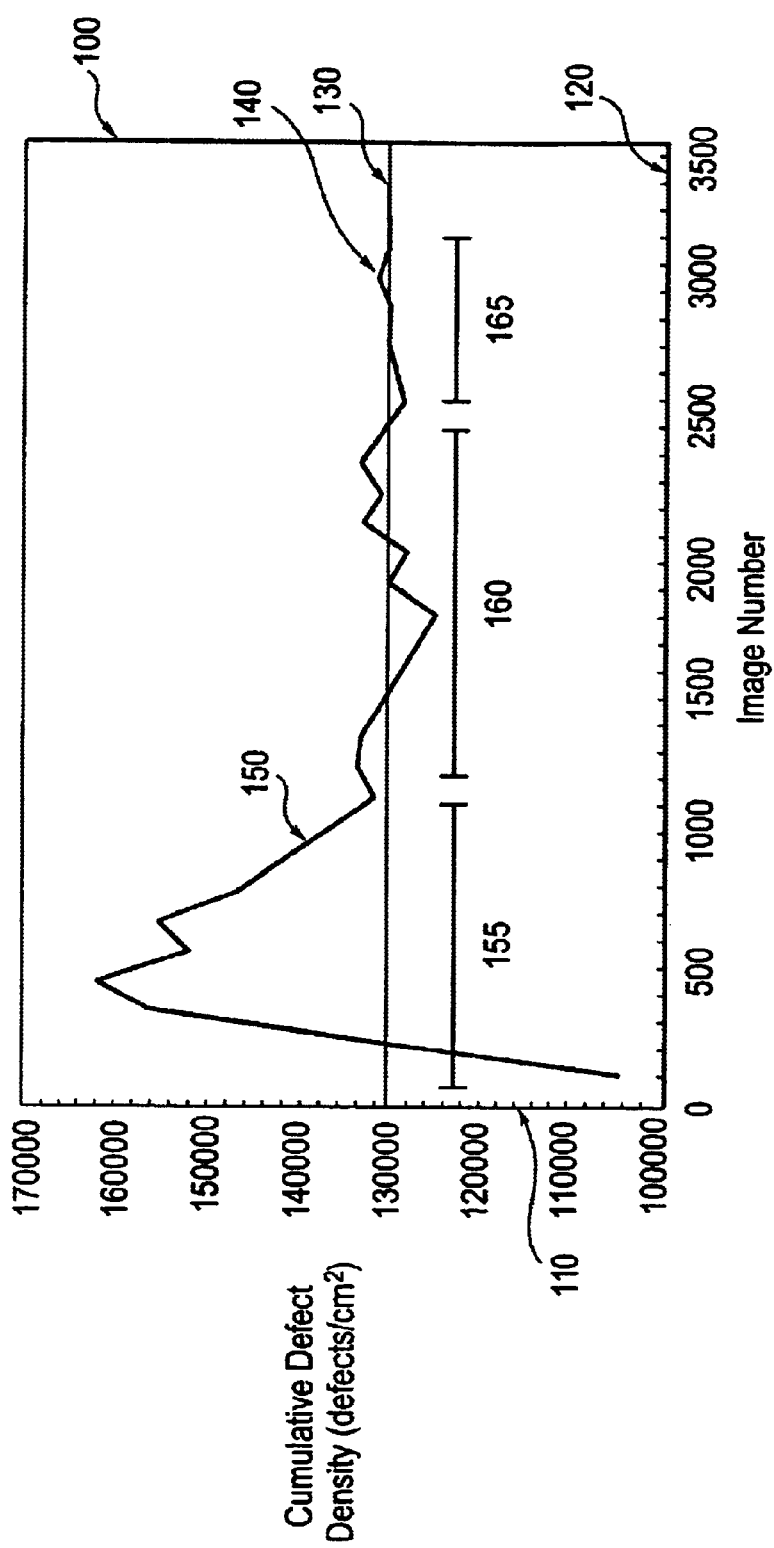
FIG. 1 is a graph of cumulative defect density data versus image number collected during an inspection made a according to a preferred embodiment of the present invention.

In accordance with a preferred embodiment of the present invention FIG. 1 depicts an example graph of cumulative defect density 100 produced during the inspection of a subsection of one example of a micro-fabricated structure, a semiconductor wafer with partially manufactured. In another embodiment of the present invention a complete integrated circuit die would undergo inspection.

A vertical axis 110 shows "Cumulative Defect Density in defects/cm^2" quantified from 100000 to 170000 defects/cm^2. A horizontal axis 120 shows image number from 0 to 3500. Each increment on the horizontal axis 120 represents a single image (hence the term "image number") taken sequentially during an automated e-beam inspection run or job. The inspection was stopped at approximately image 3100 using the statistical method of the present invention. The dotted line 130 represents the average cumulative defect density at the point when the inspection was terminated 140. The solid line or curve 150 represents the Cumulative Defect Density (CDD) curve or the incremental CDD so far calculated at each point (or representative points) along the line based on all the defect data collected from the start of the defect inspection process and up to each point in the graph.

Section lines 155, 160, 165 designate different segments or inspection time periods of line 150. During segment 155, the CDD is varying rapidly. This is because at this point during the inspection, the data collected thus far is not statistically representative of the average defect density and the CDD calculation is inevitably very sensitive to localized variations in defect locations and distributions. Variations are caused by the random distribution of the defects and because the total area inspected or the total statistical sample of defects up to this point is too small to make a reliable estimate of the overall or average defect density.

During segment 160, the rate and amplitude of variation of the CDD line 150 is substantially smaller. This is because the inspected area or sample size is now large enough that local random variations in the defect density are effectively reduced by averaging from the larger sample size. Nevertheless during period 160 there is still significant statistical variation in the CDD and the data, in this case, was still not considered to be a sufficiently accurate result to be a reasonable representation of the actual defect density in the region of the wafer being inspected During segment 165, the rate and amplitude of variations of the CDD curve 150 are even smaller. It can be seen in fact that the remaining statistical variation is rather small, and may be a sufficiently accurate estimate of the defect density, depending on the application and the goal of the inspection. Based on the overall shape of the CDD curve 150 and given the assumption that there will not be a dramatic shift in the density of defects being inspected, it is likely that the value represented by line 150 is within an acceptably small error of the actual defect density, that the inspection process can be stopped. Hence given that the CDD curve 150 appears to have stabilized, further inspection is unlikely to produce a different result and inspection time can be reduced by stopping inspection based on this data.

A preferred embodiment of the present invention, uses these statistical characteristics to control and then to determine when to stop inspection, either manually or automatically, based on the statistical properties of the data collected and specific criteria entered by the system operator at the start of (or during) inspection.

The specific statistical criteria may be defined by the operator and can include one or more of the following parameters and are not limited only to these statistical parameters listed:

a minimum area to be inspected, a maximum area to be inspected, an acceptable maximum error or minimum acceptable accuracy (as measured by a deviation metric) to within which the defect density data is required to be and a minimum period of stability to ensure that the acceptable error level or better has really been achieved for a defined inspection period (absolute period or preferably relative period) or to an acceptable level of certainty.

Those of skill in the art will recognize that other statistical parameters maybe used. Note that in fact statistically speaking there is no absolute guarantee that a stable CDD curve is really a valid estimate of the overall defect density. An extreme example where CDD would not be represent a valid estimate is a case where a large number of defects are clustered in a very small area. In such a case, the CDD curve might well stabilize for a long enough period before hitting the cluster of defects and satisfy specific stopping criteria defined by the user. In general the probability of this type of error is relatively low and it can be reduced if the user sets stopping criteria conservatively (i.e. longer period of stability and smaller error levels). In spite of this limitation, the present invention is a very useful technique that allows average inspection time to be reduced substantially in cases where the statistical distribution of defects is relatively well behaved.

The "minimum area" or minimum inspection time parameter is used to ensure that at least a minimum area is inspected. This also ensures that the statistical stopping criteria are not prematurely or erroneously satisfied by for example either an area with no defects or by an area with unusually uniform defect distribution.

The "maximum area" or maximum inspection time parameter is used to ensure that the inspection stops after all the defined area has been inspected. If the defect distribution is particularly uneven, the statistical stopping criteria may never be satisfied and for a particular inspection run no time may be saved. Note this is no different than for a conventional inspection where the area to be inspected or the number of wafers to be inspected is defined by the operator before the inspection.

The "statistical stopping criteria" refers to a set of mostly numerical and statistical criteria defined or controlled by the inspection system operator that set the conditions for early termination or stopping of the inspection run. For example, the stopping criteria can be defined as a "deviation metric" such as standard deviation being within or below a certain value or in a certain range for a minimum period of time referred to as the stability period.

FIG. 2 is a table presenting progressive image numbers against a normalized standard deviation of the CDD from a particular inspection run. As depicted by the table, for each group of several hundred images, a deviation metric is calculated.

In this example, the deviation metric is a standard deviation of the CDD normalized by dividing the standard deviation by the mean defect density or arithmetic average defect density. The result is given as a percentage. Those of ordinary skill in the art will recognize and understand the statistical terminology used. Such statistics are described in a wide range of textbooks.

In preferred embodiments of the invention, before or during a defect inspection run or job, the inspection system operator or user defines specific statistical criteria that if satisfied allow the inspection run to be stopped before all the defined or programmed inspection area has been inspected. In the example depicted in FIG. 2, the statistical criteria for stopping inspection was that the normalized standard deviation be less than 1% of the mean defect density. The advantage of using the normalized standard deviation is that it allows relative rather than absolute stopping criteria. While in some situations using an absolute value of a deviation metric such as standard deviation may be convenient, in most cases the defect density of defects in the area to be inspected will not be known before inspection is complete. Hence the accuracy of the defect density estimate can only meaningfully be defined as a percentage deviation.

Figure 3:
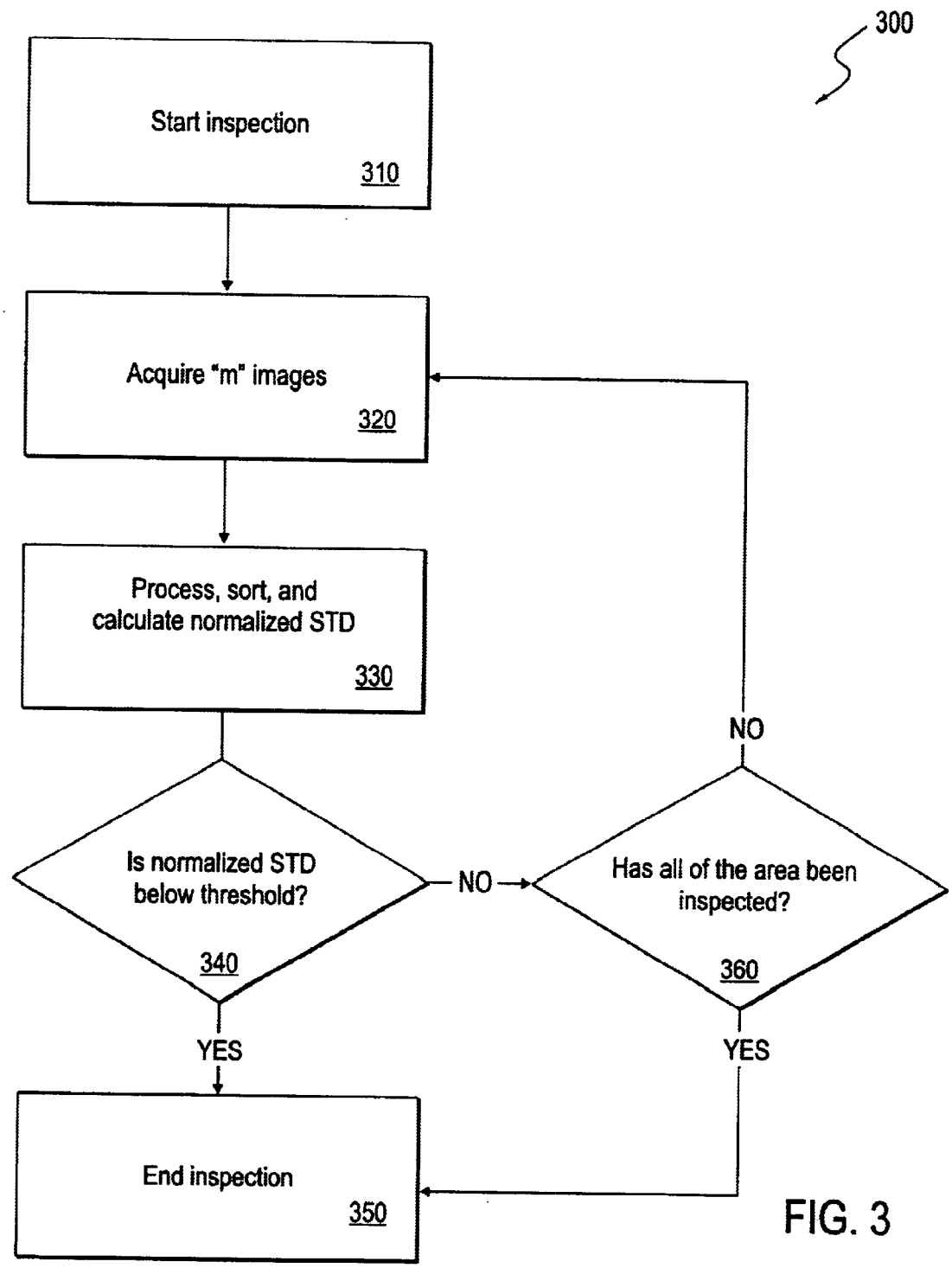
FIG. 3 is a flow diagram of a preferred embodiment of the present invention.

FIG. 3 is a flow diagram 300 of a process of a preferred embodiment of the present invention. The process starts at step 310. The inspection run is started with an inspection recipe or inspection criteria defined by the inspection system user. The user also at this point specifies inspection "stop criteria" such as a threshold value for a deviation metric. In this example, the deviation metric is a normalized standard deviation of CDD. When the normalized standard deviation is below this predefined threshold value the inspection run is terminated.

At step 320 in the process, "m" (an integer) images are acquired of the micro-fabricated structure being inspected. After each "m" images are acquired, defect data and statistics are computed and the result processed. "m" specifies a convenient interval between statistical computations and maybe defined by the user or may be a system parameter. Note in general it will be most convenient for the computation of defect data and results to be performed in parallel with the inspection for reasons of efficiency and to save time, however, this is not a requirement of this embodiment of the invention. It should also be noted that "m" in effect defines a stability period during which the CDD must be within a deviation metric of the mean defect density.

After "m" images have been acquired in step 320, the images are processed in step 330. The images are compared to a reference in order to detect defects. If more than one type of defect is being detected step 330 also includes sorting or classifying the defects by type. Various Automatic Defect Classification (ADC) systems and software packages (also referred to as Coarse Defect Binning) are available for performing this classification from Schlumberger Technologies, Inc, KLA-Tencor and Applied Materials of Santa Clara, Calif.

Defect density data and statistics including a deviation metric are also calculated during step 320 and in particular a normalized standard deviation (STD) is calculated.

At step 340 the normalized standard deviation is compared to the predefined user threshold. If the normalized standard deviation is less than the user defined threshold the process goes to step 350 where the inspection run is ended as the stopping criteria for early termination of inspection have been satisfied. If the normalized standard deviation is greater than (or equal to) the predefined threshold the process goes to step 360.

At step 360 in the process, a test is performed to determine whether or not all of the defined area to be inspected has in fact already been inspected. If all the defined area has been inspected, then again the process goes to step 350 and inspection is terminated. If area still remains to be inspected the process returns to step 320 where another "m" images will be acquired.

In summary, this process will continue round the process loop defined by steps 320, 330, 340 & 360 until either all the area to be inspected has been inspected or until the normalized standard deviation is below the user defined threshold.

Figure 4:
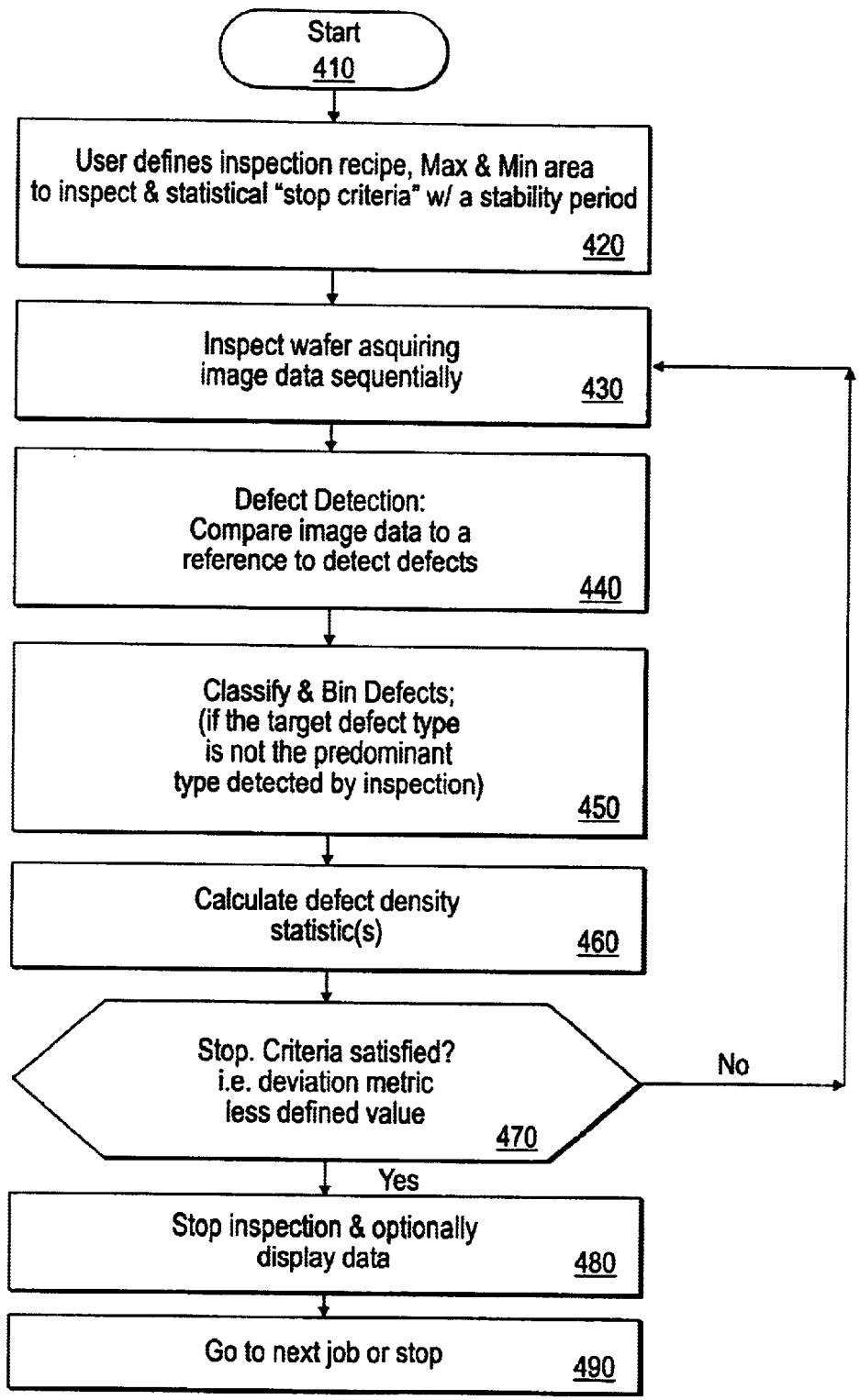
FIG. 4 is a detailed flow diagram of a method of using the invention.

FIG. 4 depicts a more detailed flow diagram 400 of an alternate preferred embodiment of the invention. The process starts at step 410. At step 420 the user defines an inspection recipe for the inspection system being used. During step 420 the user also defines a maximum inspection area and statistical "stop criteria" or a condition for stopping inspection before the maximum inspection area has been completed. The stop criteria comprises:

A minimum area of the micro-fabricated structure to be inspected: The purpose of this minimum area is to ensure that at least a certain portion of the structure is inspected and thus the minimum area in effect defines a minimum statistical sample for the inspection run.

A deviation metric: The deviation metric is the statistical error below which the statistic of interest, in this case CDD, must be within of a reference statistic, in this case the mean or arithmetic average defect density in order to stop the inspection run.

A stability period: the stability period defines the period of the inspection that the CDD must be within the deviation metric of the reference statistic before inspection may be terminated. The stability period can be defined as an absolute time period, or an absolute area of the inspection or can be defined as a relative value such as a percentage of the inspection time so far or the percentage inspection area so far. (Note that the percentage time or area may not be equivalent as some inspection systems vary the inspection speed depending upon the number of defects being detected or the speed of an ADC software package may also slow inspection).

The maximum area defines an upper limit for the area of the micro-fabricated structure to be inspected. The purpose of the maximum area of the micro-fabricated structure is simply to ensure that inspection stops at a defined point if statistical criteria to stop inspection early are not met, e.g. when the defect distribution is heavily skewed and a meaningful single defect density estimate cannot be made within the criteria specified.

The inspection run is started at step 430 and the inspection system acquires pixilated contrast data usually combined to form images for convenience. Data is acquired sequentially according to the inspection system defined recipe and usually sequentially over the area to be inspected.

At step 440, defect detection is performed. A range of different defect inspection algorithms are in common use depending upon the inspection technology and the vendor of that technology. Typically pixilated contrast or image data is compared to reference data (either predefined reference data or data acquired from similar neighboring structures such as neighboring cells or die on a semiconductor wafer) to detect defects. The location of detected defects is recorded as defect data often constructed as a visual defect map showing the location of individual defects or of clusters of defects (not shown).

At step 450 defect data is optionally classified or binned based on defect image characteristics such as shape, size, color, grayscale, center of gravity, etc. Commercial automatic defect classification (ADC) software packages are available as already referenced.

At step 460 defect density statistics are calculated including CDD, a deviation metric such as absolute, relative or normalized deviation or standard deviation.

At step 470 the stopping criteria are reviewed. In this embodiment, if the minimum area has been inspected, and the deviation metric is within the predefined range and has stayed within that range for the predefined stability period, then the process moves to step 480. At step 480 the inspection run is stopped and the data optionally displayed.

At step 470 if the stop criteria have not been met, the process is directed to step 430 to continue the inspection process. Note that the inspection will also progress to step 480 after step 470 if the maximum inspected area has been completed.

At step 490 the process looks for a next inspection job or wafers. If additional jobs or wafers are available the process is repeated. If no additional jobs or wafers are available the inspection process is complete and stops.

Figure 5:
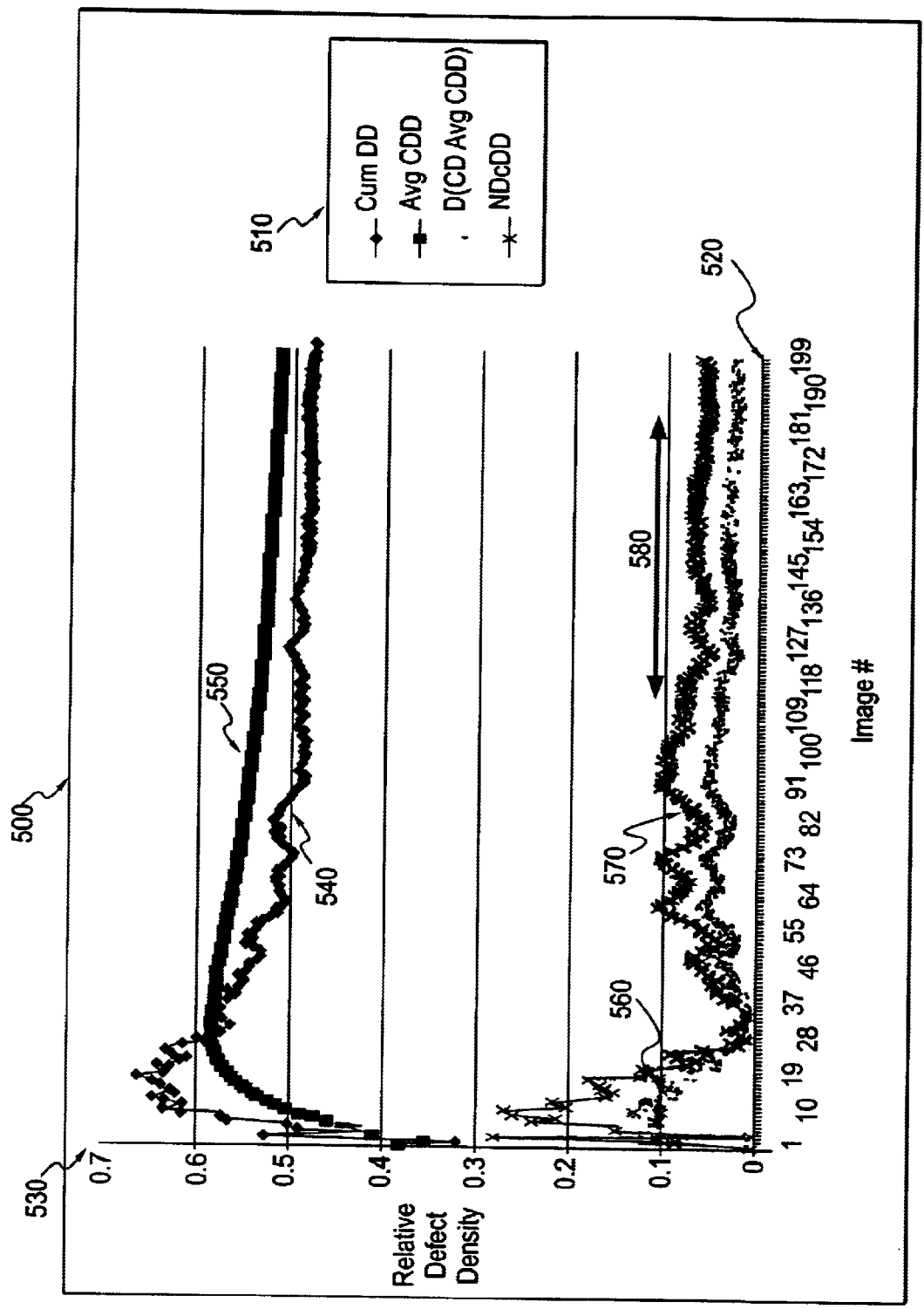
FIG. 5 is a graph depicting results of an example of a simulated cumulative defect density with the corresponding derived statistics.

FIG. 5 is a graph 500 depicting results of an example of a simulated cumulative defect density (CDD) 540 with the corresponding derived statistics represented as data lines 550, 560, 570. Graph 500 has legend 510 depicting the symbols for each of the data lines 540, 550, 560, 570. Axis 520 is the X or horizontal graph axis and represents simulated defect image number in the range 1 to 199. Y or vertical axis represents "Relative Defect Density" in the range from 0 to 0.7 in arbitrary units.

Data line 540 represents the CDD calculated from a simulation of a defect inspection run with a random distribution of defects generated by a commercially available random number generator such as that in Microsoft Corporation of Redmond, Wash., Excel spreadsheet software. Each point on data line 540 was calculated by dividing the total number of simulated defects detected up to each point in the graph by the simulated area inspected up to that point. Data line 540 corresponds to the diamond symbol in legend 510 with abbreviated legend label "Cum DD". Data line 540 shows initially relatively large swings in value which die down at approximately image #100 and becomes relatively stable from approximately image #100 to image #199.

Data line 550 represents the incremental average of the cumulative defect density calculated from the simulated CDD from the start up to each point. Data line 550 corresponds to the square symbol in legend 510 with abbreviated label "Avg CDD". Data line 550 shows initially a relatively large swing that is an averaged or smoothed version of CDD data line 540.

Data line 560, represented by the triangle symbol in legend 510 with abbreviated label "D(CD Avg CDD)" depicts the absolute difference or delta between the CDD data line 540 and the average CDD line 550. Data line 570, represented by the "X" symbol in legend 510 with abbreviated label "NDcDD", depicts the normalized version of the difference or delta between the CDD and average CDD date lines. The normalization of delta CDD 570 is calculated by dividing the absolute difference values in data line 560 by the average CDD 550. Either the normalized delta CDD 570 or the absolute delta CDD 560 can be used as the deviation metric in stopping an inspection with specific stopping criteria. Generally the normalized deviation metric is preferred as absolute deviation is dependent on the overall defect density that is unknown at the start of the inspection.

This simulation example illustrates one preferred embodiment of the statistical calculations required to determine that a sufficiently stable value of CDD or defect density has been achieved and that an inspection run can be terminated early, before the maximum area defined for the inspection run has been completed. In this example, statistical stop criteria can be the deviation metric (i.e. either the absolute or normalized CDD, 560 and 570 respectively) combined with a minimum stability period represented by arrow 580. The specific criteria for stopping the simulated inspection run early were that the normalized delta CDD 570 should be less than 0.1 for a period of at least one third of the inspection run as illustrated by arrow 580 with a minimum inspected area to be at least 100 images.

Figure 6:
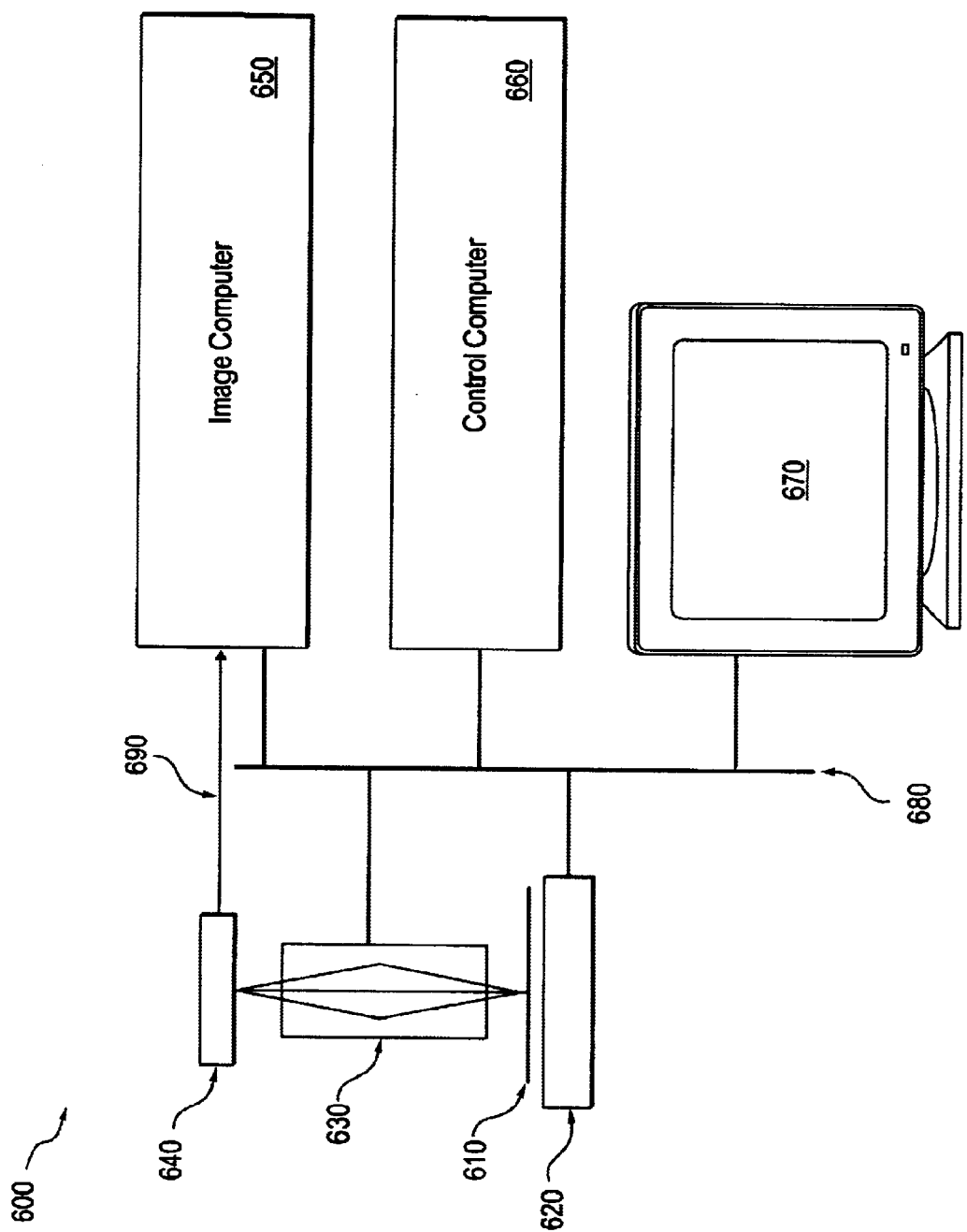
FIG. 6 is a schematic block diagram of a preferred embodiment of the present invention.

FIG. 6 is a schematic block diagram 600 of a preferred embodiment inspection system according to the present invention. Wafer 610 is positioned on XY stage 620 usually by wafer handling robotics, not shown (preferably including a vacuum load-lock in the case of an e-beam or charged particle beam inspection system). Microscope 630 is integrated with detector means subsystem 640 and images wafer 610 to supply a pixelated image signal to image computer 650 by connection means 690 (preferably including an Analog-to-Digital Converter, not shown). Microscope 630 can be an optical microscope including optical bright field, optical dark field, optical gray field, UV or a laser scatter system or microscope 630 can be a charged particle microscope such as an e-beam, voltage contrast or focused ion-beam. Detector means subsystem 640 for an optically-based microscope examples include CCD, TDI, CMOS, Vidicon tube image sensor or MCP-based image intensifier or PMTs in the case of a laser scatter system. Detector means subsystem 640 for a charged particle beam-based microscope examples include a scintillator and photo-multiplier combination or other electron multiplying device, a MCP or Micro-Channel Plate, or a solid state semiconductor detector such as a PIN or other avalanche diode device. Connection means 690 examples include a wire or multiple wires in parallel preferably configured for fast analog or digital data transfer or an optical fiber or multiple optical fibers in parallel each including an analog-to-digital converter.

Image computer 650 uses stored program instructions or other predetermined arithmetic processing hardware to process the image signal to detect defects in wafer 610. This processing usually comprises comparing the image signal data with pre-stored reference images. The reference images can be from similar structures on the wafer 610 or can be from a similar wafer or can be from a database including a design database. Defects are detected as the differences between the acquired images and the reference images. Defect locations are recorded as defect data which can be displayed on display means 670. When the defect data contains data on more than one defect type, the stored program instructions can optionally include automatic defect classification software to classify the defect data by defect type. Defect data density statistics can then be calculated for at least one classified defect type.

Control computer 660 controls the whole system over control and data bus 680. Control computer 660 periodically through an inspection run calculates statistics of the defect data such as defect density, cumulative defect density, a deviation metric between the defect density and the cumulative defect density such as standard deviations. The control computer 660 continues the inspection process while the deviation metric statistic is outside a user-defined range and stops inspection when the deviation metric is within the user-defined range.

When a particular inspection run has been stopped by satisfying the user-defined stopping criteria in this manner, data can optionally be displayed on display means 670 and the next inspection run on the present or another wafer can be started.

Note that the specific inspection run examples presented show relatively high defect densities from a single wafer or part thereof, however, this statistical approach to saving inspection time is equally applicable and valuable to inspection runs comprised of multiple wafers.

Although the foregoing is provided for purposes of illustrating, explaining and describing certain embodiments of the defect inspection efficiency improvement with in-situ statistical analysis of defect data during inspection in particular detail, modifications and adaptations to the described method and other embodiments will be apparent to those skilled in the art and may be made without departing from the scope or spirit of the invention.

What is claimed is:

1. A method of optimizing inspection of micro-fabricated structures by statistically analyzing defect data during inspection, the method comprising:
   a. collecting defect data during inspection;
   b. calculating at least one statistic of the defect data;
   c. continuing inspection while the at least one statistic is outside a predetermined range and
   d. stopping inspection when the at least one statistic is within the predetermined range.

2. The method of claim 1 where the collecting defect data step is performed with an e-beam inspection system.

3. The method of claim 1 where the at least one statistic is a standard deviation of a defect density of the defect data.

4. The method of claim 1 where the at least one statistic is a standard deviation of a cumulative defect density.

5. A method of reducing defect inspection time of micro-fabricated structures by statistically analyzing defect data during inspection, the method comprising:
   a. inspecting the micro-fabricated structures by acquiring pixelated contrast data from the micro-fabricated structures;
   b. detecting defects in the micro-fabricated structures by comparing the pixelated contrast data with reference data to create the defect data;

c. calculating at least one statistic of the defect data;

d. continuing inspection while the at least one statistic is outside a predetermined range and e. stopping inspection when the at least one statistic is within the predetermined range.

6. The method of claim 5 further comprising after the stopping inspection step, displaying the defect data.

7. The method of claim 5 where the inspecting step is performed with an e-beam inspection system.

8. The method of claim 5 where the at least one statistic is a standard deviation of a defect density of the defect data.

9. The method of claim 5 where the at least one statistic is a standard deviation of a cumulative defect density.

10. A method of reducing defect inspection time of micro-fabricated structures by statistically analyzing defect data during inspection, the method comprising:

a. inspecting the micro-fabricated structures by acquiring pixilated contrast data from the micro-fabricated structures;

b. detecting defects in the micro-fabricated structures by comparing the pixilated contrast data with predetermined reference data to create the defect data;

c. classifying the defect data into at least one classified defect type;

d. calculating at least one defect density of the at least one classified defect type;

e. determining a deviation metric of the at least one defect density of the at least one classified defect type;

f. continuing to inspect the micro-fabricated structures while the deviation metric is outside a predetermined range and g. stopping inspection when the deviation metric is within a predetermined range.

11. The method of claim 10 where the inspecting step is performed with an e-beam inspection system.

12. The method of claim 10 where the deviation metric is a standard deviation of the at least one defect density of the at least one classified defect type.

13. The method of claim 10 where the deviation metric is a standard deviation of an at least one cumulative defect density of the at least one classified defect type.

14. A method for reducing average defect inspection time by statistically analyzing defect data in near real-time from a semiconductor wafer during defect inspection, the method comprising:

a. inspecting the semiconductor wafer to detect defects by acquiring image data of integrated circuit die on the semiconductor wafer;

b. processing the image data to detect defects in the integrated circuit die to create the defect data;

c. classifying the defect data into at least one classified defect type;

d. calculating at least one defect density of the at least one classified defect type;

e. determining a deviation metric of the at least one defect density of the at least one classified defect type;

f. continuing inspection while the deviation metric is outside a predetermined range;

g. stopping inspection when the deviation metric is within the predetermined range.

15. The method of claim 14 where the inspecting step is performed with an e-beam inspection system.

16. The method of claim 14 where the inspecting step is performed with a UV inspection system.

17. The method of claim 14 where the deviation metric is a standard deviation of the at least one defect density of the at least one classified defect type.

18. The method of claim 14 where the deviation metric is a standard deviation of an at least one cumulative defect density of the at least one classified defect type.

19. An efficient wafer defect inspection system comprising:

an XY stage disposed to support a wafer for inspection;

a microscope disposed to generate image data of the wafer;

a detector arranged to supply image data of the wafer from the microscope to an image computer;

stored program instructions that execute on the image computer to produce defect data of defects on the wafer;

a control computer disposed to control the inspection system, the control computer periodically calculating at least one statistic of the defect data and the control computer stopping inspection when the at least one statistic is within a predetermined range.

20. The inspection system of claim 19 wherein the microscope is an e-beam-based microscope.

21. The inspection system of claim 19 wherein the at least one statistic is a standard deviation.

22. The inspection system of claim 19 wherein the at least one statistic is a standard deviation of an at least one cumulative defect density of the defect data.

* * * * *